(12) United States Patent
Larabee (10) Patent No.: US 9,168,548 B2
(45) Date of Patent: *Oct. 27, 2015

(54) LIQUID DISPENSING DEVICE

(71) Applicant: Eric Stephen Larabee, Bellevue, WA (US)

(72) Inventor: Eric Stephen Larabee, Bellevue, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/281,497

(22) Filed: May 19, 2014

(65) Prior Publication Data

US 2014/0252126 A1    Sep. 11, 2014

Related U.S. Application Data

(63) Continuation of application No. 12/660,115, filed on Feb. 22, 2010, now Pat. No. 8,727,181.

(60) Provisional application No. 61/209,655, filed on Mar. 10, 2009.

(51) Int. Cl.
*B67D 7/84* (2010.01)
*B65F 7/00* (2006.01)
*B05B 7/24* (2006.01)
(Continued)

(52) U.S. Cl.
CPC .............. *B05B 7/2408* (2013.01); *A61L 2/22* (2013.01); *A61L 11/00* (2013.01); *B65F 7/00* (2013.01); *A61L 2202/23* (2013.01); *Y10T 29/49826* (2015.01)

(58) Field of Classification Search
CPC ............ B05B 11/0005; B05B 11/3001; B05B 11/0037; B05B 11/3056; B65D 47/121; B65D 25/00; B65D 83/222; B65F 1/06; B65F 7/00

USPC ................ 222/1, 160, 162, 156–159, 153.01, 222/153.04, 153.11, 153.13, 238, 192, 222/402.1, 321.7; 220/908, 908.1, 908.2, 220/87.1–87.2; 366/156.1

See application file for complete search history.

(56) References Cited

U.S. PATENT DOCUMENTS

| | | |
|---|---|---|
| 1,481,685 A | 1/1924 | Burrows |
| 2,281,630 A | 5/1942 | Southard |
| 2,652,173 A | 9/1953 | Farrell |

(Continued)

OTHER PUBLICATIONS

U.S. Appl. No. 12/660,115, Non-Final Office Action mailed Mar. 23, 2012.

(Continued)

*Primary Examiner* — Frederick C Nicolas (74) *Attorney, Agent, or Firm* — Kilpatrick Townsend & Stockton LLP (57) ABSTRACT

A liquid dispensing device for a trash container spray system may be provided. In accordance with at least one embodiment, the liquid dispensing device is activated upon the trash receptacle being lifted and placed back on the ground, moving a piston and actuator component of the liquid dispensing device from a first to second position, back to the first position, and providing the force needed to spray the liquid compound into the interior of the trash receptacle. In accordance with at least one embodiment, a manually activated pump feature may be provided for spraying a liquid compound into the interior of a trash receptacle via the liquid dispensing device. In accordance with at least one embodiment, a float valve feature may be provided for spraying the liquid compound into the interior of the trash receptacle via the liquid dispensing device.

20 Claims, 9 Drawing Sheets

(51) Int. Cl.
*A61L 2/22* (2006.01)
*A61L 11/00* (2006.01)

(56) References Cited

U.S. PATENT DOCUMENTS

| | | |
|---|---|---|
| 3,307,902 A | 3/1967 | Laura |
| 3,372,875 A | 3/1968 | Torrey |
| 3,636,862 A | 1/1972 | Bottas et al. |
| 3,921,857 A | 11/1975 | Riccio |
| 4,902,482 A | 2/1990 | Faust |
| 4,907,747 A | 3/1990 | Kim |
| 5,104,230 A | 4/1992 | Douche |
| 5,170,903 A | 12/1992 | Fleming |
| 5,366,122 A | 11/1994 | Guentert et al. |
| 5,829,642 A | 11/1998 | Momboisse |
| 5,964,229 A | 10/1999 | Brendel |
| 6,845,888 B2 | 1/2005 | Verherbrugghen et al. |
| 7,516,865 B1 | 4/2009 | Pierre |
| 7,878,359 B1 | 2/2011 | Ko |
| 8,727,181 B2 * | 5/2014 | Larabee ........................ 222/162 |

OTHER PUBLICATIONS

U.S. Appl. No. 12/660,115, Final Office Action mailed Feb. 8, 2013.
U.S. Appl. No. 12/660,115, Ex parte Quayle Action mailed Sep. 17, 2013.
U.S. Appl. No. 12/660,115, Notice of Allowance mailed Jan. 9, 2014.

* cited by examiner

LIQUID DISPENSING DEVICE

CROSS-REFERENCES TO RELATED APPLICATIONS

This application is a continuation of U.S. application Ser. No. 12/660,115, filed on Feb. 22, 2010, titled "LIQUID DISPENSING DEVICE" issuing as U.S. Pat. No. 8,727,181 on May 20, 2014, and claims the benefit of U.S. Provisional Application Ser. No. 61/209,655, filed on Mar. 10, 2009, titled "LIQUID DISPENSING DEVICE," the contents of each are hereby incorporated in their entirety by reference.

BACKGROUND OF THE INVENTION

The use of large bins or containers for the deposit of trash and/or garbage from commercial establishments and residential apartments has grown substantially. These trash or garbage containers are usually emptied periodically by a front loading dump truck which carries a pair of forwardly extending lift forks that are insert able into pick up sleeves placed on opposed sides of the containers so that the container can be lifted off the ground and its contents dumped into the body of the truck. Since these containers are quite large, they may not be emptied for a substantial period of time such as a week or more in some instances. Because these containers often receive garbage as well as trash, many municipalities have required that the interior of the container be treated periodically with a treating material such as a disinfectant and/or odor suppressor. Even when not required by statute, such treatment of the containers is a desirable service which users of the containers may request form the company which supplies and services the containers.

Most front loading containers are presently sprayed by the driver of the truck who, after the trash or garbage has been emptied, must leave the cab of the truck, unwind a hose attached to a spray tank of insecticide and/or odor suppressor, spray the interior of the container, rewind the hose, and return to the cab of the truck. A suitable spray tank and hose arrangement for performing this task is shown in U.S. Pat. No. 3,372,875 to Torrey. It will be readily apparent that there are a number of drawbacks to the presently available container treatment systems. Since the truck may empty 60 to 100 trash or garbage containers during a single day, the driver must perform this procedure many times. The task soon becomes onerous and often is not performed as thoroughly as it should be. The time involved is also substantial and may consume an additional hour or more which could be spent on servicing other customers. The driver is also subject to repeated exposures to the material being sprayed onto the containers and such exposure is at least unpleasant and may be detrimental to the health of the driver. The customer either must have a spray treatment of the trash containers to comply with local statutes or desires this service for reasons of sanitation, but the driver who must perform the service views it as a time consuming, tiresome, disagreeable chore, thus causing a continuous controversy between the customer and the trash containing servicing contractor over the performance of the service.

BRIEF SUMMARY OF THE INVENTION

A method and apparatus are provided for a trash container spray system, and more particularly, a container spray system for selectively spraying a variety of cleaning materials into a commercial trash container.

DETAILED DESCRIPTION OF THE INVENTION

Techniques described and suggested herein include an apparatus and method for providing a liquid dispensing device for a trash container spray system. In accordance with at least one embodiment, the liquid dispensing device may be coupled with a trash container. The liquid dispensing device may include a delivery system for providing a liquid compound to the inside of the trash container. In accordance with at least one embodiment, the liquid dispensing device may spray the inside of a trash container when the trash container is upended and placed back on a surface. In accordance with at least one embodiment, the liquid dispensing device may include a manually operated pump to initiate the spraying process. In accordance with at least one embodiment, a plurality of liquid dispensing devices may be coupled together to provide a combination of various disinfecting or cleaning liquids to the inside of a trash container. In accordance with at least one embodiment, the multiple liquid dispensing devices could be installed in a master/slave arrangement to aid in the delivery of multiple compounds into the trash container.

In accordance with at least one embodiment, the liquid dispensing device may include a variety of nozzles for different spray delivery patterns. A particular spray pattern, such as a mist spray pattern, may be optimal for certain trash containers depending on the liquid being delivered and the material being stored in the container. In accordance with at least one embodiment, the liquid dispensing device may include multiple reservoirs and nozzles for the simultaneous delivery of several liquid compounds to the inside of the trash container.

In accordance with at least one embodiment, the liquid dispensing device may be accompanied by a water level sensor or float valve. The water level sensor/float valve could activate the liquid dispensing device when the water level in a container reaches a particular threshold. For example, an insect repellant could be delivered to the inside of the trash container upon the water reaching a certain level to prevent breeding grounds for insects such as mosquitoes. In accordance with at least one embodiment, the liquid dispensing device may be externally coupled or internally coupled with the trash container while still providing a liquid to the inside of the trash container.

In accordance with at least one embodiment, the liquid dispensing device may be comprised of any combination of plastic, resin, plastic resin, synthetic resin, acrylonitrile butadiene styrene (ABS), thermoplastic, a polycarbonate composition, elastomer composition, or metallic composition. The use of plastic or plastic resin may provide for a more durable liquid dispensing device while maintaining a lower manufacturing cost. However, other material compositions for the liquid dispensing device may be appropriate depending upon the waste material disposed of in the trash container and the liquid compound being delivered to the inside of the trash container. In accordance with at least one embodiment, the liquid dispensing device may include a locking mechanism for preventing the spraying of liquid while the trash container is being transported. Activating the lock mechanism on the liquid dispensing device would allow for the transportation of a trash container, where the trash container may be upended and placed back on a surface, without spraying the inside of the trash container with the stored liquid compound.

It is an object of the claimed invention to provide an improved trash container by adding a spray system to a trash container. The trash container includes a base, a lid arranged opposite the base, and at least one sidewall extending up from the base. The base and lid and sidewall enclose an interior of the container, and the container is shaped and adapted to temporarily hold items for subsequent removal by lifting the receptacle from a support service and upending the receptacle.

Figure 1:
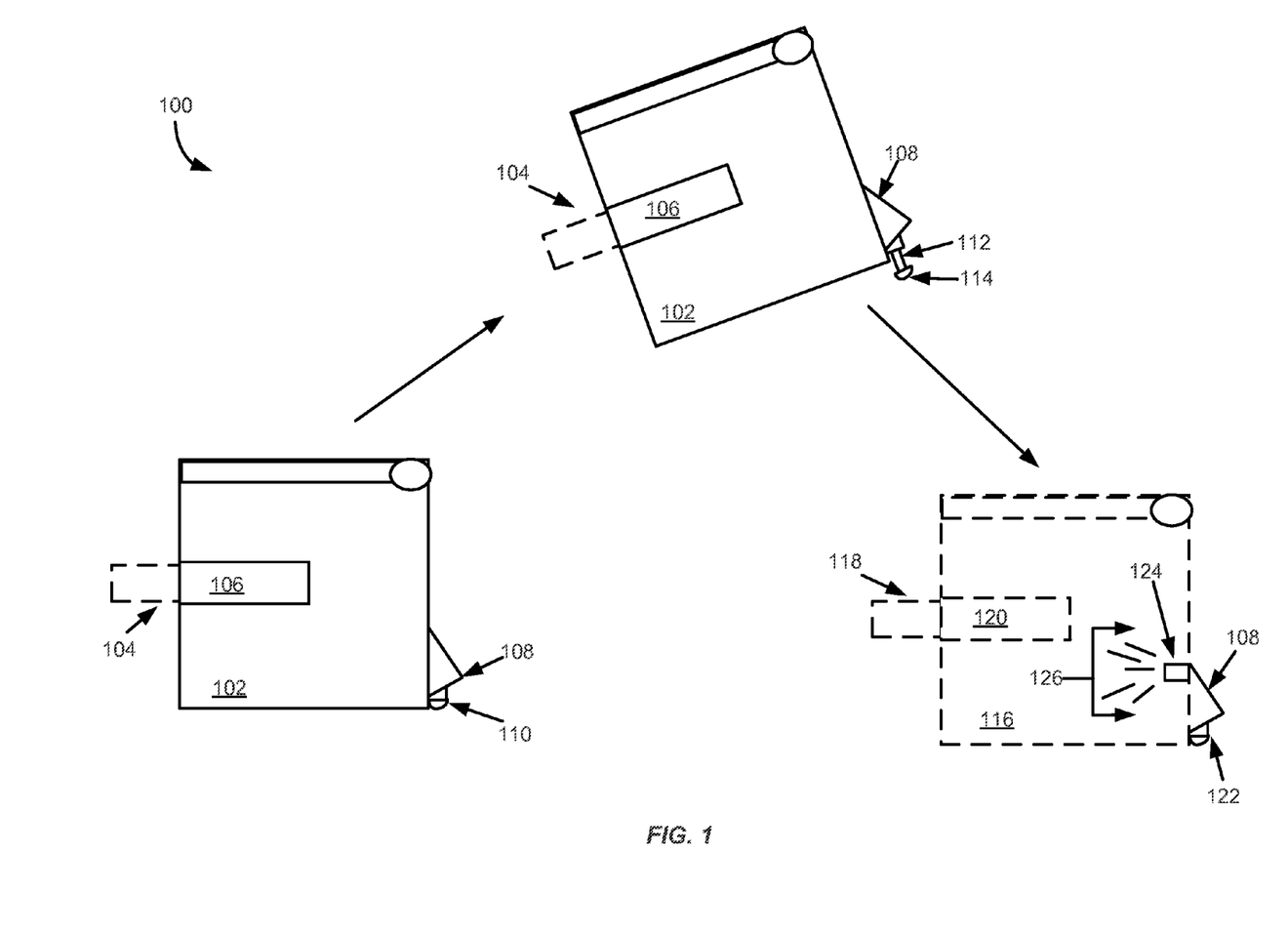
FIG. 1 is a flow diagram that illustrates an example of a trash container spray system including a liquid dispensing device and a trash receptacle in accordance with at least one embodiment.

FIG. 1 is a flow diagram 100 that illustrates an example of a liquid dispensing device in a trash container spray system in accordance with at least one embodiment. The flow diagram 100 includes a trash container 102 with a lifting tine 104 from a garbage truck inserted into a sleeve 106 of the trash container 102. An example liquid dispensing device 108 is coupled with the trash container 102. The liquid dispensing device 108 includes a piston and actuator component 110 in a first position. In accordance with at least one embodiment, as the trash container 102 is lifted by, for example a garbage truck, the liquid dispensing device 108 is primed by gravity to spray a liquid compound inside of the trash container. A lifted trash container 102 is included in FIG. 1. Trash container 102 is lifted in the air by the lifting tine 104 by a garage truck via the sleeve 106. The liquid dispensing device 108 includes a piston 112 and actuator 114 that is decompressed, into a second position, from the liquid dispensing device 108 through gravity as the trash container 102 is lifted from the ground.

In accordance with at least one embodiment, the decompression of the piston 112 and actuator 114 primes a spraying reservoir within the liquid dispensing device 108. FIG. 1 includes an internal view of the trash container 102 as shown in 116, as the garbage truck places the trash container 116 back on the ground via the lifting tine 118 and sleeve 120, the piston 112 and actuator 114 of the liquid dispensing device 108 are compressed, back into the first position as shown in 122, thus forcing a liquid compound into the inside of the trash container 116. In accordance with at least one embodiment, the force of placing the trash container 116 on the ground compresses the piston 112 and actuator 114 forcing liquid via a channel within the liquid dispensing device 108 through a nozzle 124 which results in a spray 126 that covers the inside of the trash container 116 with a liquid compound. In accordance with at least one embodiment, the actuator 114 may be comprised of a plastic resin composition or metallic ball bearing which allows for smooth transportation of trash containers along a surface. As described above, the nozzle 124 may include a variety of suitable liquid dispensing nozzles for delivering different spray patterns to the inside of a spray container.

Figure 2:
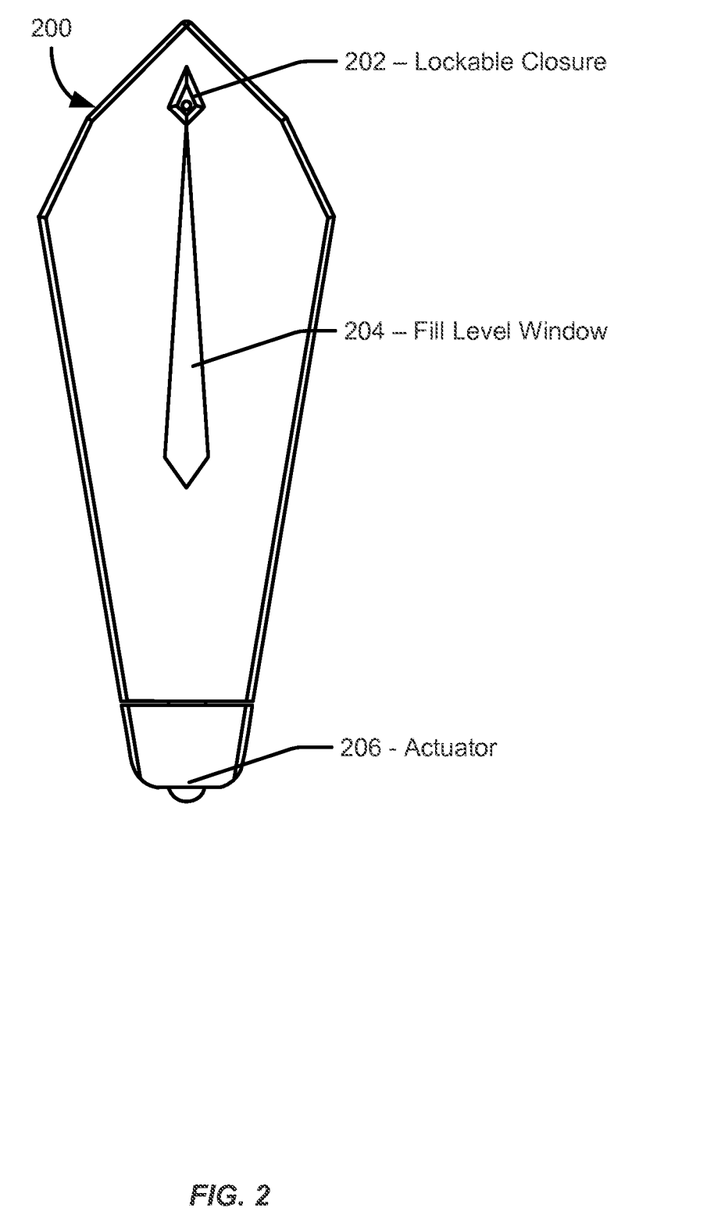
FIG. 2 illustrates a schematic diagram depicting an exterior view of a liquid dispensing device in accordance with at least one embodiment.

FIG. 2 illustrates a schematic diagram depicting an exterior view of a liquid dispensing device in accordance with at least one embodiment. FIG. 2 includes a liquid dispensing device 200 that includes a lockable closure 202, a fill level window 204, and the actuator 206 in a first position (compressed). In accordance with at least one embodiment, the lockable closure 202 can be used to close a channel within the liquid dispensing device 200 to prevent spraying liquid into the trash container when moving the trash container. Thus, while the actuator and piston components of the liquid dispensing device may move from a first position to a second position and back to a first position, the liquid would not be expelled from the nozzle but stay in the channel. In accordance with at least one embodiment, the fill level window 204 can provide an indication of a current level of the liquid in the reservoir. A user can use this window to gauge when more liquid compound will need to be provided to the liquid dispensing device for future uses. In accordance with at least one embodiment, the actuator houses is coupled with a piston (not shown) and extends or decompresses upon the liquid dispensing device being lifted in the air as described above in FIG. 1.

Figure 3:
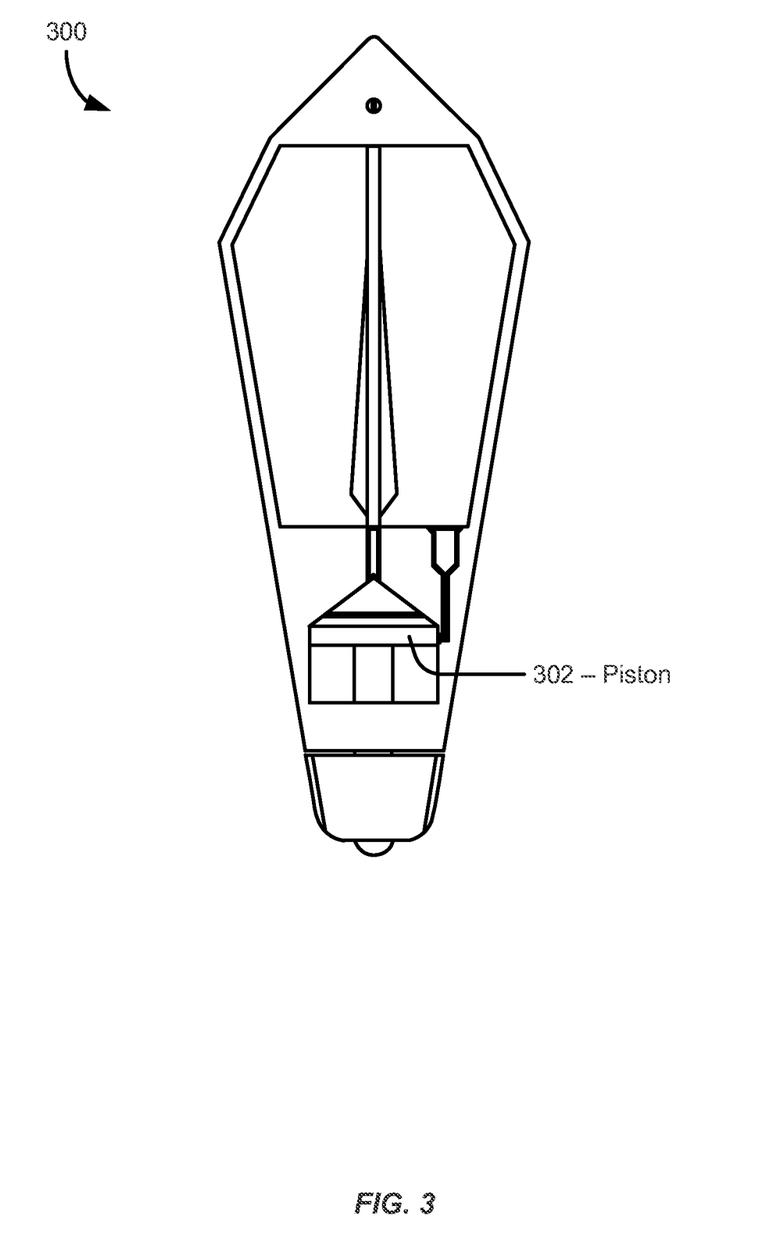
FIG. 3 illustrates a schematic diagram depicting an interior view of a liquid dispensing device in accordance with at least one embodiment.

FIG. 3 illustrates a schematic diagram depicting an interior view of a liquid dispensing device 300 in accordance with at least one embodiment. The liquid dispensing device 300 includes a piston 302 that is coupled with the actuator and reservoir of the liquid dispensing device. In accordance with at least one embodiment, the length of the piston 302 and surrounding sprayer body or piston chamber determines the amount of pay load dispensed through the nozzle of the liquid dispensing device. Different configurations of piston and sprayer body can result in different amounts of liquid compound being delivered into the interior of a trash container, depending on the waste being dealt with and the size of the container.

Figure 4:
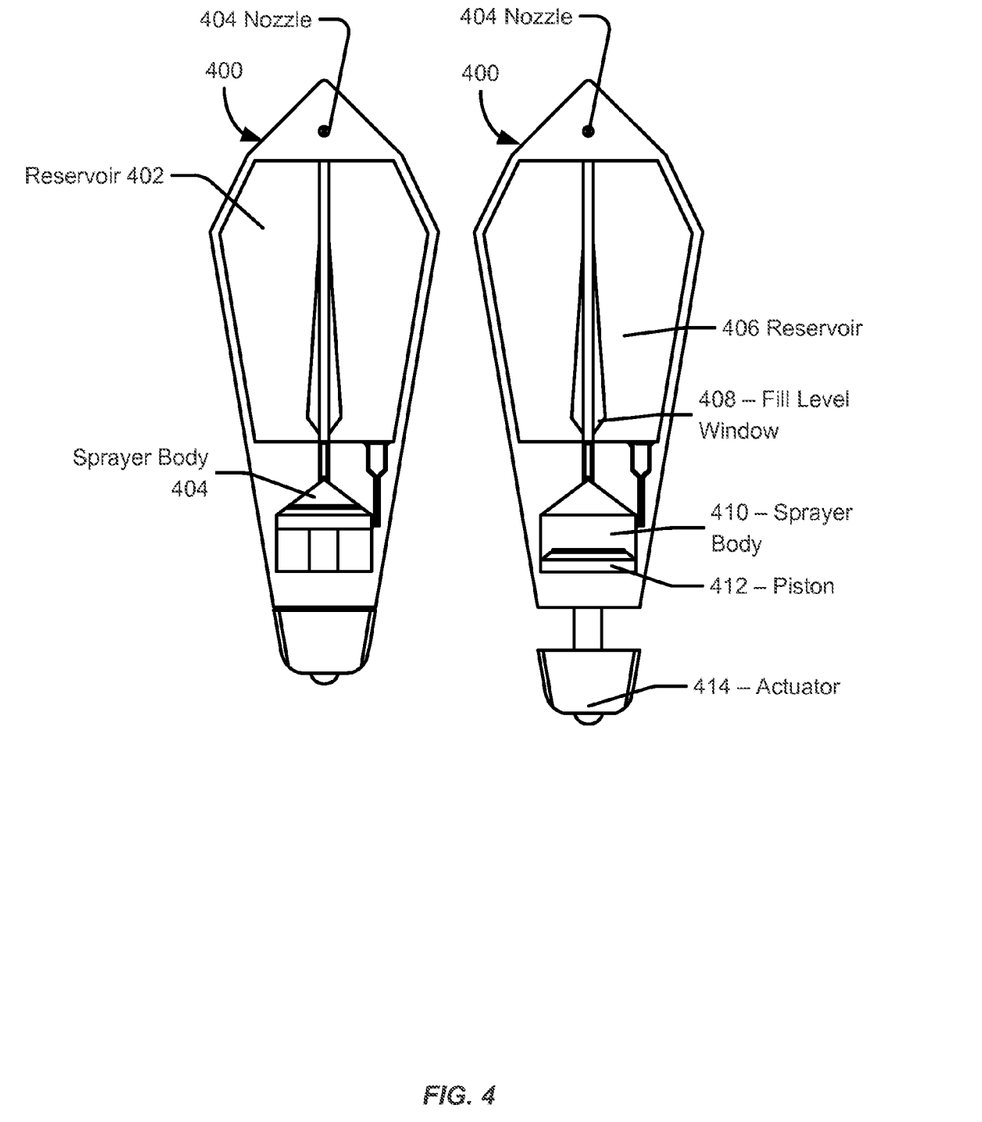
FIG. 4 illustrates a schematic diagram depicting an interior view of a liquid dispensing device, including a first and second position of a piston and actuator component of the liquid dispensing device in accordance with at least one embodiment.

FIG. 4 illustrates a schematic diagram depicting an interior view of a liquid dispensing device 400, including a first and second position of a piston and actuator component of the liquid dispensing device in accordance with at least one embodiment. The interior view of the liquid dispensing device 400, in a first, compressed position, includes a reservoir 402 and a sprayer body 404. The sprayer body 404 is in liquid communication with the reservoir 402 and a nozzle 404 is in liquid communication with the reservoir 402. The liquid dispensing device 400 illustrated in a second position includes a nozzle 404, a reservoir 406, a fill level window 408, a sprayer body 410, a piston 412, and actuator 414. In accordance with at least one embodiment, the actuator 414 has a biasing mechanism and a contact plate. The contact plate is operatively connected to the piston 412 and the biasing mechanism is operatively connected to the contact plate. The contact plate is shaped and adapted to contact a support surface when a trash container is placed on the support surface and the piston 412 and biasing mechanism is shaped and adapted to move between the first and the second position as described above.

The piston 412 and biasing mechanism are further shaped and adapted to extend the piston 412 and contact plate away from the base of the trash container when the trash container is removed from the support surface (as described in FIG. 1), and to retract the piston 412 and contact plate when the container is replaced on the support surface (FIG. 1). The actuator 414 is shaped and adapted to draw liquid from the reservoir 402, 406 into the sprayer body 404, 410 when the piston 412 is moved in a direction from the first position toward the second position and to expel liquid from the sprayer body 404, 410 toward the nozzle 404 when the piston 412 is moved in a direction from the second position toward the first position. The nozzle 404 is shaped and adapted to spray a liquid on at least a portion of the interior of a trash container or receptacle.

Figure 5:
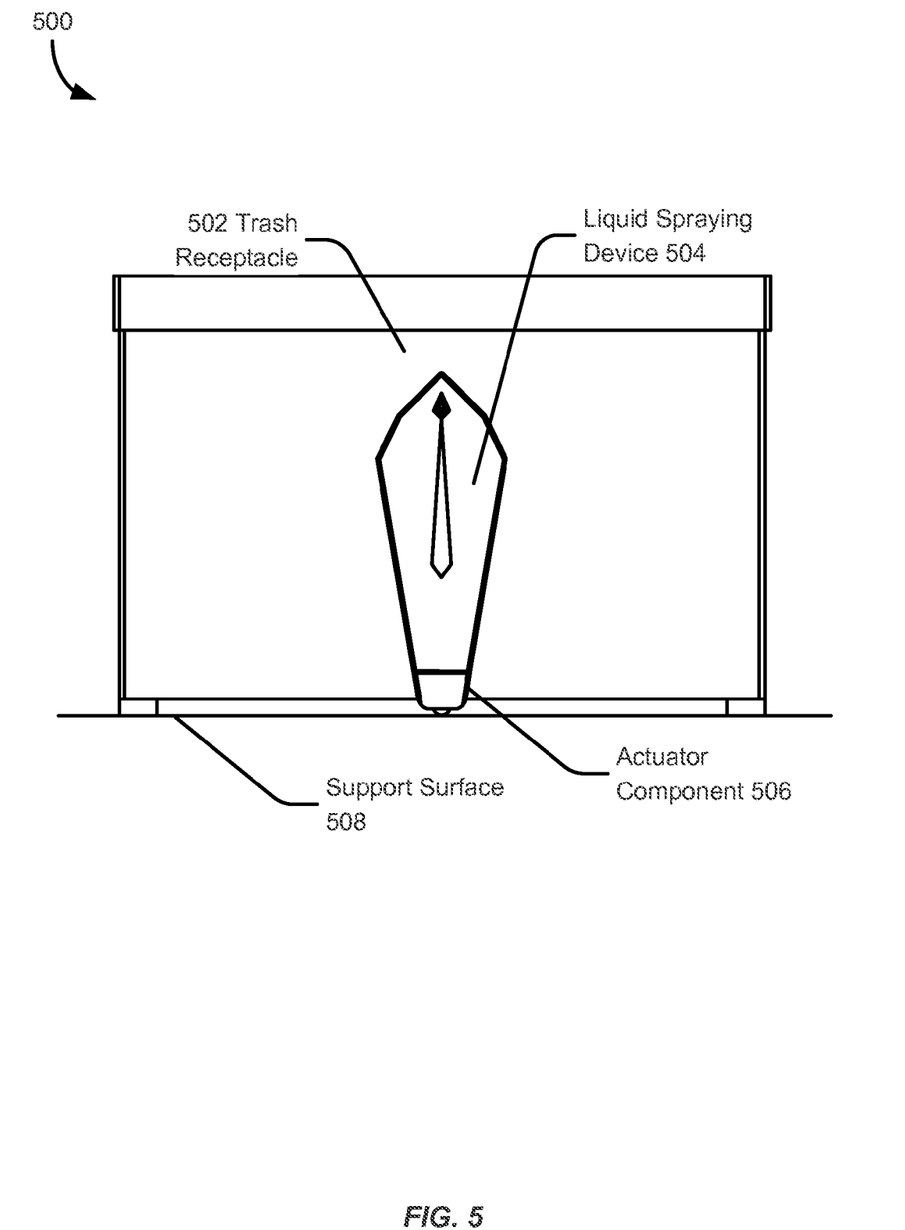
FIG. 5 illustrates a liquid dispensing device communicatively coupled to a trash receptacle in accordance with at least one embodiment.

FIG. 5 illustrates a liquid dispensing device coupled with a trash receptacle in accordance with at least one embodiment. Included in FIG. 5 is the trash receptacle 502, liquid spraying device 504, and actuator component 506. As described above, the liquid spraying device 504 is eternally coupled with the trash receptacle 502. The actuator component 506 is in contact with a support surface 508. The actuator component 506 may be curved or rounded to allow for smooth transportation of the trash receptacle 502 and liquid spraying device 504 across the support surface 508.

Figure 6:
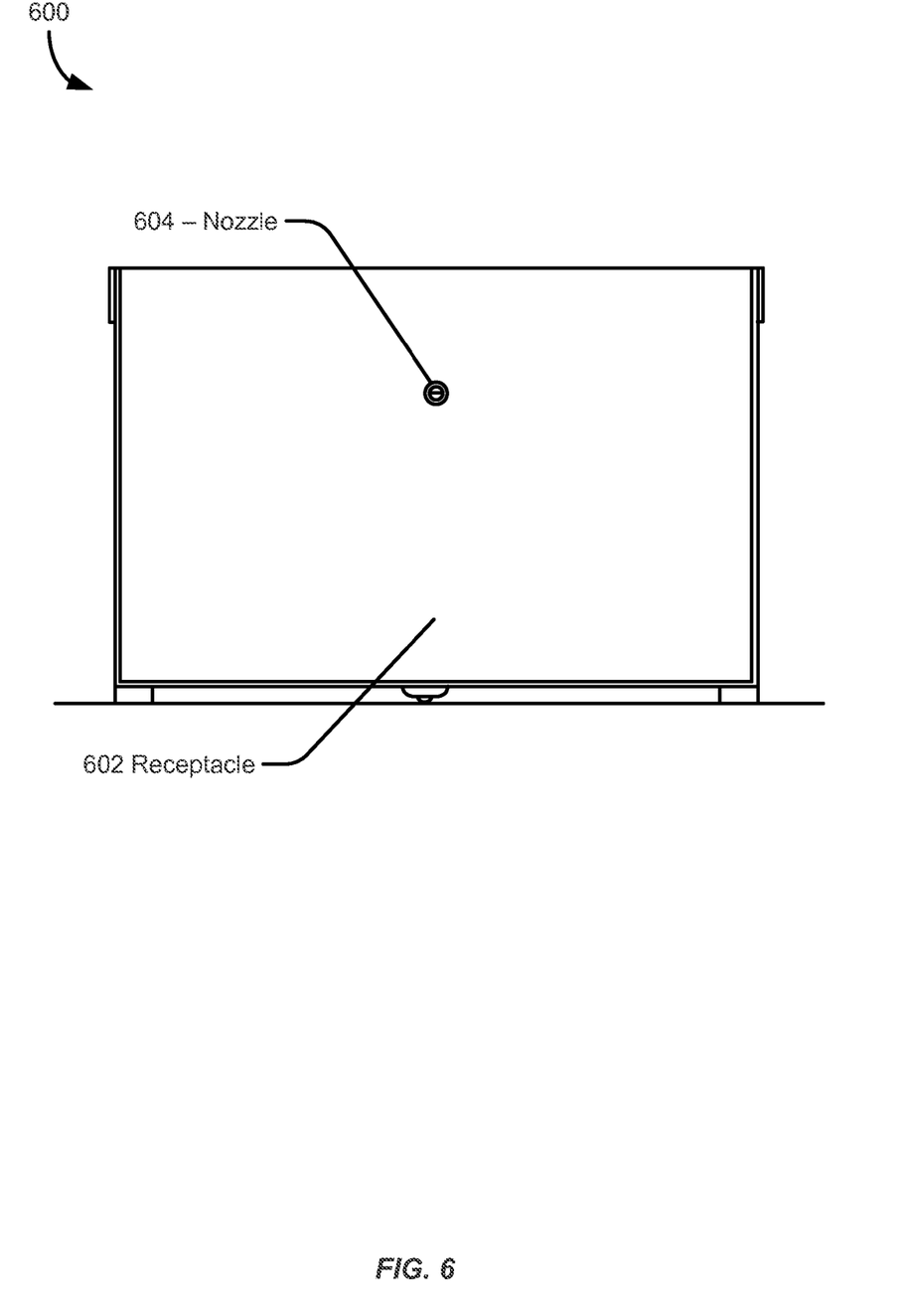
FIG. 6 illustrates a schematic diagram depicting interior aspects of a nozzle of a sprayer body and trash receptacle in accordance with at least one embodiment.

FIG. 6 illustrates a schematic diagram depicting interior aspects of a nozzle of a sprayer body and trash receptacle in accordance with at least one embodiment. The interior aspect of the trash receptacle 602 includes a nozzle 604. The configuration illustrated in FIG. 6 is not meant to be limiting and as described above the liquid dispensing device can be coupled with the trash receptacle 602 via the interior of the trash receptacle 602. The configuration illustrated in FIG. 6 however includes the liquid dispensing device being exteriorly coupled with the trash receptacle 602 with only the nozzle 604 of the liquid dispensing device being in communication with the interior of the trash receptacle 602. In accordance with at least one embodiment, the liquid dispensing device delivers a liquid compound to the interior of the trash receptacle 602 via the nozzle 604.

Figure 7:
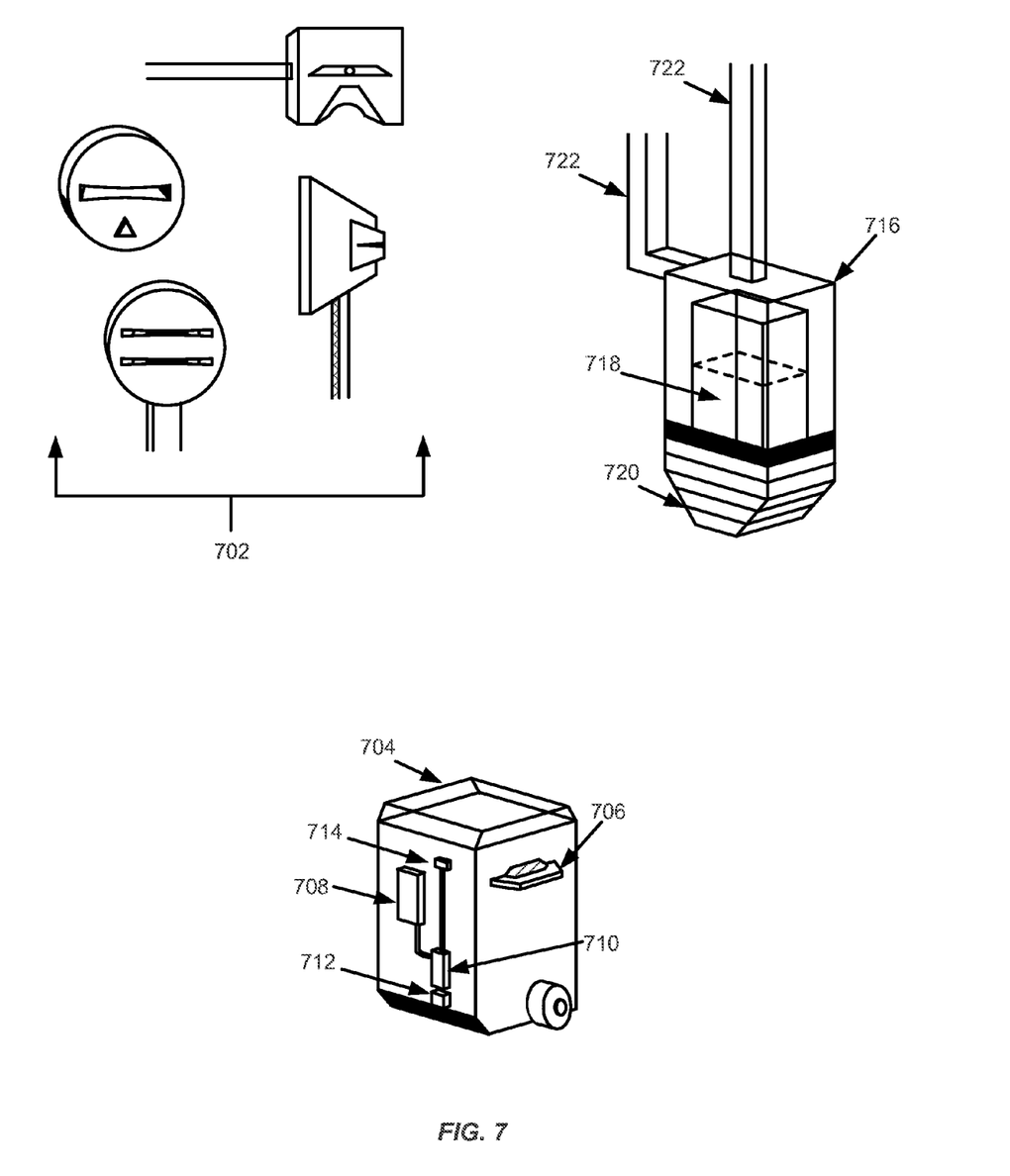
FIG. 7 illustrates several examples of nozzle types for the liquid dispensing device, an exterior view of a liquid dispensing device coupled to a trash receptacle, and a multi-channel liquid reservoir for a liquid dispensing device in accordance with at least one embodiment.

FIG. 7 illustrates several examples of nozzle types for the liquid dispensing device, an exterior view of a liquid dispensing device coupled to a trash receptacle, and a multi-channel liquid reservoir for a liquid dispensing device in accordance with at least one embodiment. The several examples of nozzle types 702 included in FIG. 7 would each result in a different spray pattern in the interior of a trash container depending on the pressure exerted by the liquid dispensing device and the properties of the liquid compound. In accordance with at least one embodiment, the nozzle types can be easily interchanged with the liquid dispensing device. Included in FIG. 7 is a trash container 704, a sleeve or lifting handle 706, a liquid reservoir 708 that is in liquid communication with the liquid dispensing device 710. The liquid dispensing device 710 also includes the actuator and piston component 712 and, in the current configuration, an externally housed nozzle 714. The externally housed nozzle 714 however is still in liquid communication with the interior of the trash container 704. It should be appreciated that the configuration of the trash container spray system as illustrated in features 704-714 is not meant to be limiting and the liquid dispensing device 710 may be configured in multiple ways to achieve the delivery of a liquid compound as described herein.

FIG. 7 includes a liquid dispensing device 716 that includes a reservoir 718, an actuator 720, and a multi-channel liquid configuration 722. As described briefly above, the liquid dispensing device 716 is capable of delivering a liquid compound to multiple nozzles that are in liquid communication to the interior of a trash container. The multi-channel configuration may be appropriate for the delivery of different liquid compounds from the liquid dispensing device 716, or to cover a larger trash container. In accordance with at least one embodiment, the reservoir 718 may be segmented into multiple reservoirs, each dispensing liquid to a different channel and nozzle to spray the interior of a trash container.

Figure 8:
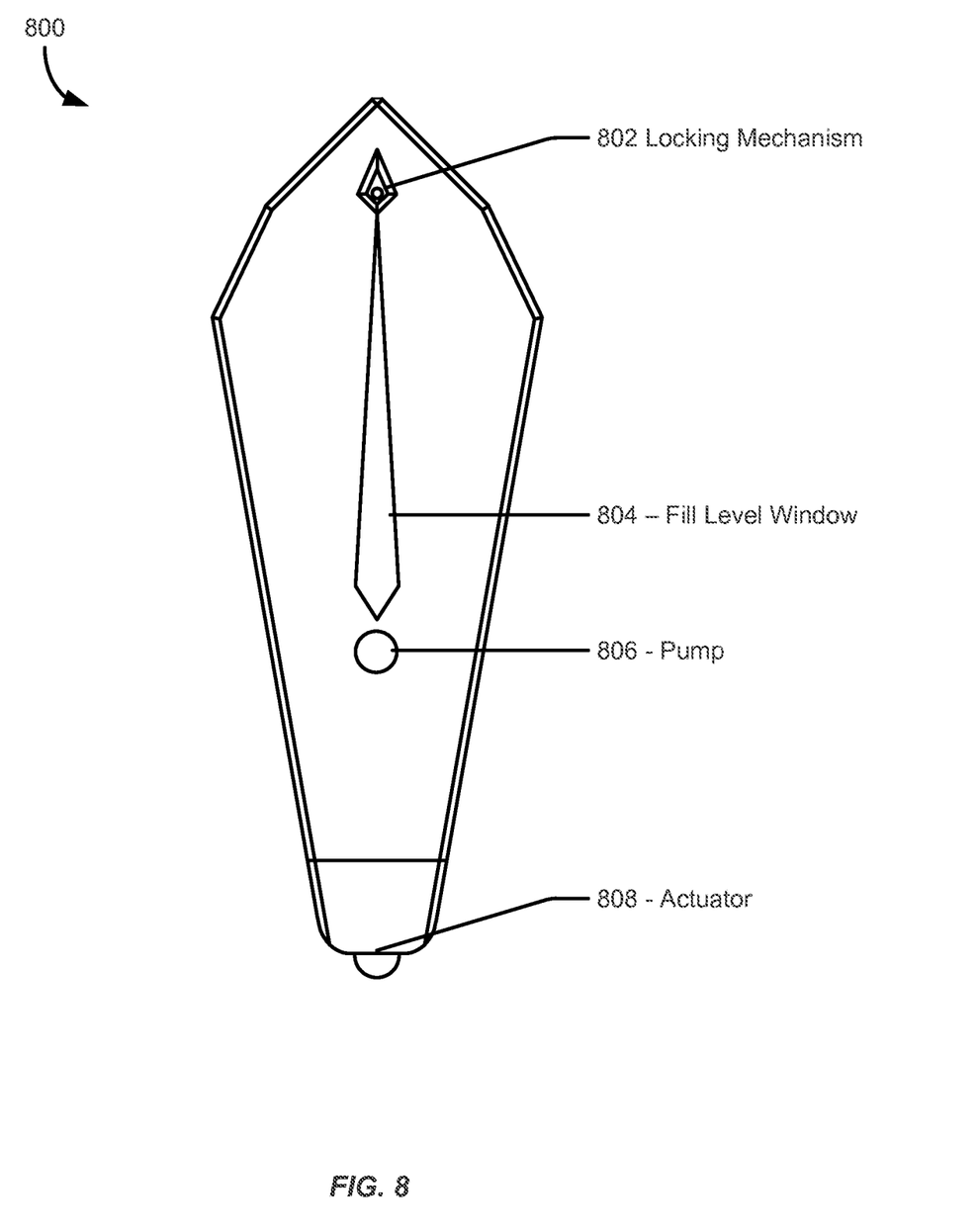
FIG. 8 illustrates a schematic diagram depicting exterior aspects of a liquid dispensing device including a locking mechanism and pump feature in accordance with at least one embodiment.

FIG. 8 illustrates a schematic diagram depicting exterior aspects of a liquid dispensing device including a locking mechanism and pump feature in accordance with at least one embodiment. The liquid dispensing device 800 of FIG. 8 includes a locking mechanism 802 (similar to lockable closure 202), a fill level window 804, a pump 806, and an actuator 808. In accordance with at least one embodiment, the liquid dispensing device 800 may include a pump 806 that can be used at the operators discretion for spraying liquid to the interior of a trash container. The pump 806 may be a hand operated squeeze ball pump. The squeeze ball pump may be in liquid communication with a secondary reservoir of the liquid dispensing device 800 which can be used to pump the liquid compound through the liquid dispensing device and nozzle into the receptacle. In accordance with at least one embodiment, the liquid compound is drawn into the pump from the secondary reservoir as the pump is extended expanding the bladder. When the user needs to dispense the liquid compound into the trash receptacle they forcibly compress the pump thus pushing the liquid from the pump into a channel dispensing the liquid through the nozzle of the liquid dispensing device. In accordance with at least one embodiment, the squeeze ball consists of a bladder made from a semi rigid material. When the user squeezes the squeeze ball pump the fluid with in the pump, that is in liquid communication with the secondary reservoir is forced out transferring liquid through the nozzle. Releasing the bladder creates a draw from the secondary reservoir replenishing the fluid back into the pump. This constitutes the entire pump cycle. Valves can be incorporated into the system to adjust the flow and transfer of fluids if needed.

Figure 9:
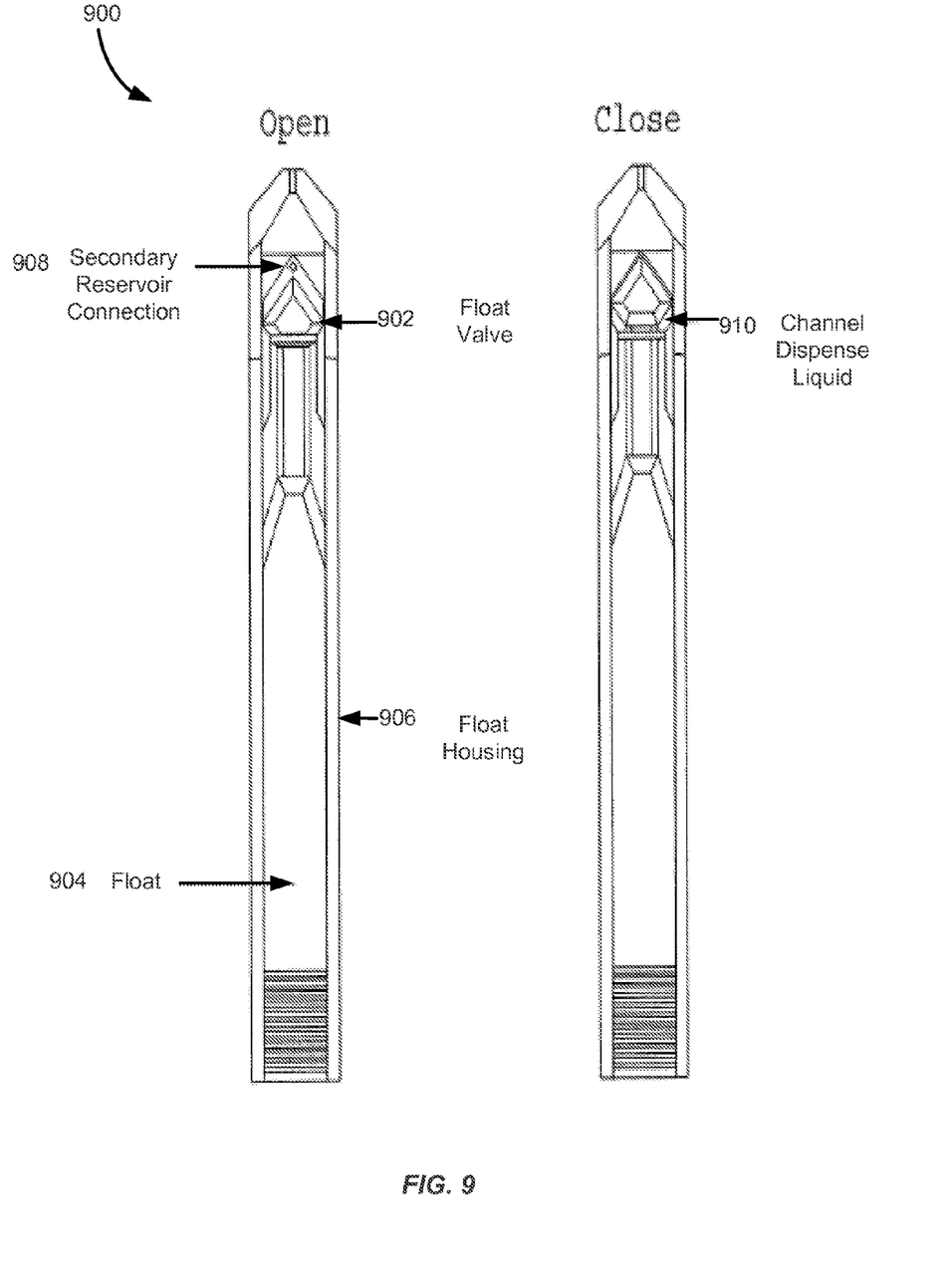
FIG. 9 illustrates a schematic diagram depicting interior aspects of a float valve feature including an open and close position of a float valve in accordance with at least one embodiment.

FIG. 9 illustrates a schematic diagram depicting interior aspects of a float valve feature including an open and close position of a float valve in accordance with at least one embodiment. FIG. 9 includes a float valve feature 900. In accordance with at least one embodiment, the liquid dispensing device may have a float valve 902 incorporated into the system to dispense liquid when the float valve measures a certain levels of liquid with in the receptacle. This gravity float valve would work or be utilized when the liquid level inside the receptacle has measured a predetermined depth, possibly a result of rain. At this point the liquid with in the device is released into the interior of the receptacle. This feature may help with mosquito control as well as other problems that are a direct result of excessive moisture.

In accordance with at least one embodiment, the float valve 902 is directly attached to a sealed float 904. This sealed float 904 component sits with in a float housing body 906 attached with in the interior of the receptacle at a predetermined height off the bottom surface of the receptacle. The float valve 902 at the open position is gravity set against the seal inhibiting liquid from the devices secondary reservoir to pass through the secondary reservoir connection 908 above the float valve 902.

In accordance with at least one embodiment, when a certain amount of liquid is accumulated within the receptacle the float 904 will begin to float on top of the liquid with in the receptacle. At this point the float valve 902 rises upward to a close position allowing the liquid within the secondary reservoir to be released through channels 910 below the valve seat into the interior of the receptacle the liquid dispensing device is attached. The float valve 902 also works as a shut off system when the float is at its highest position. Liquid cannot be transferred through the secondary reservoir. As the liquid level with in the receptacle drops, the float 904 will drop to its open position and reset the float valve 902. This constitutes the entire float valve cycle.

What is claimed is:

1. A liquid spraying device, comprising:
   a sprayer body interfacing with a trash receptacle, the trash receptacle including a base in contact with a support surface;
   a reservoir in liquid communication with the sprayer body, the reservoir configured to hold a liquid;
   at least one nozzle in liquid communication with the sprayer body and projecting from the sprayer body into the trash receptacle; and
   an actuator having a piston, the actuator configured to contact the support surface, the piston configured to move between a first and second position, wherein the piston is further configured to move from the first position to the second position upon the trash receptacle being removed from the support surface, the piston configured to extend away from the base of the trash receptacle upon movement between the first position to the second position, the actuator configured to draw the liquid from the reservoir in response to the piston moving in a direction from the first position to the second position and further configured to provide the liquid via the at least one nozzle to an interior of the trash receptacle upon the piston moving in a direction from the second position to the first position.

2. The liquid spraying device of claim 1, further comprising a lockable closure located on the reservoir.

3. The liquid spraying device of claim 1, further comprising a fill level window located on the reservoir for displaying a current level of the liquid in the reservoir.

4. A liquid spraying device comprising:
   a sprayer body configured to interface with a trash receptacle that includes at least a base in contact with a support surface;
   a reservoir in liquid communication with the sprayer body, the reservoir configured to store a liquid;
   a nozzle configured to project to an interior of the trash receptacle, the nozzle being in liquid communication with the sprayer body; and
   an actuator-piston mechanism configured to move between a first position and a second position, wherein the first position comprises the actuator-piston mechanism being in contact with the support surface, wherein the second position comprises the actuator-piston mechanism extending away from the base of the trash receptacle in response to the trash receptacle being removed from the support surface, the actuator-piston mechanism further configured to prime the reservoir to provide the liquid to the interior of the trash receptacle in response to the actuator-piston moving from the first position to the second position, and to provide the liquid to the interior of the trash receptacle in response to the actuator-piston moving from the second position to the first position.

5. The liquid spraying device of claim 4, further comprising:
   a second reservoir in liquid communication with the sprayer body, the second reservoir configured to store the liquid; and
   a pump configured to interface with the sprayer body and in liquid communication with the second reservoir, wherein the pump is further configured to dispense the liquid via the nozzle to the interior of the trash receptacle in response to a user forcibly compressing the pump.

6. The liquid spraying device of claim 5, wherein the pump further comprises a bladder configured to contract and expand in response to pressure.

7. The liquid spraying device of claim 4, wherein the trash receptacle includes a commercial trash dumpster configured to be lifted by a trash truck.

8. The liquid spraying device of claim 4, wherein the sprayer body is comprised of at least one of a plastic, a resin, a plastic resin, a synthetic resin, an acrylonitrile butadiene styrene (ABS), a thermoplastic, a polycarbonate composition, an elastomer composition, or a metallic composition.

9. The liquid spraying device of claim 4, further comprising an interface configured to accept a plurality of nozzles, an individual nozzle of the plurality of nozzles having a different spray pattern for providing the liquid to the interior of the trash receptacle.

10. The liquid spraying device of claim 4, further comprising a plurality of sprayer bodies configured to interface with the trash receptacle, the plurality of sprayer bodies arranged in a master/slave configuration to provide different liquids via the nozzle to the interior of the trash receptacle, an individual sprayer body of the plurality of sprayer bodies comprising an individual reservoir configured to store a different liquid.

11. A method comprising:
    providing a liquid spraying device, the liquid spraying device configured to operatively attach to a trash receptacle, the trash receptacle including a base in contact with a support surface, the liquid spraying device comprising a reservoir, a sprayer body in liquid communication with the reservoir, a nozzle in liquid communication with the sprayer body and the reservoir, and an actuator having a piston, the reservoir configured to store a liquid and in liquid communication with the sprayer body, the actuator and the piston configured to move between a first position and a second position;
    in response to removing the trash receptacle from the support surface:
       moving the piston from the first position to the second position to prime the actuator for providing the liquid from the reservoir to an interior of the trash receptacle; and
    in response to placing the trash receptacle on the support surface:
       moving the piston from the second position to the first position causing the actuator to provide the liquid from the reservoir via the nozzle to the interior of the trash receptacle.

12. The method of claim 11, wherein the liquid spraying device further comprises a float housing body, a float, a float valve, and a second reservoir, the float housing body configured to attach to the interior of the trash receptacle, the float housing body in liquid communication with the second reservoir, the second reservoir in liquid communication with the sprayer body, the float valve configured to move between an open position and a close position based at least in part on the float, the float configured to move vertically within the float housing based on a liquid level within the interior of the trash receptacle, the float valve further configured to provide a different liquid, stored within the second reservoir, to the interior of the trash receptacle based on the movement between the open position and the close position of the float valve.

13. The method of claim 11, wherein the liquid spraying device further comprises a lockable closure located on the reservoir.

14. The method of claim 11, wherein the liquid spraying device further comprises a fill level window located on the reservoir for displaying a current liquid level in the reservoir.

15. The method of claim 11, wherein the liquid spraying device further comprises:
 a second reservoir in liquid communication with the sprayer body, the second reservoir configured to store the liquid; and
 a pump configured to interface with the sprayer body and in liquid communication with the second reservoir, wherein the pump is further configured to dispense the liquid via the nozzle to the interior of the trash receptacle in response to a user forcibly compressing the pump.

16. The method of claim 15, wherein the pump further comprises a bladder configured to contract and expand in response to pressure.

17. The method of claim 11, wherein the trash receptacle includes a commercial trash dumpster configured to be lifted by a trash truck.

18. The method of claim 11, wherein the sprayer body is comprised of at least one of a plastic, a resin, a plastic resin, a synthetic resin, an acrylonitrile butadiene styrene (ABS), a thermoplastic, a polycarbonate composition, an elastomer composition, or a metallic composition.

19. The method of claim 11, wherein the liquid spraying device further comprises an interface configured to accept a plurality of nozzles, an individual nozzle of the plurality of nozzles having a different spray pattern for providing the liquid to the interior of the trash receptacle.

20. The method of claim 11, wherein the liquid spraying device further comprises a plurality of sprayer bodies configured to interface with the trash receptacle, the plurality of sprayer bodies arranged in a master/slave configuration to provide different liquids via the nozzle to the interior of the trash receptacle, an individual sprayer body of the plurality of sprayer bodies comprising an individual reservoir configured to store a different liquid.

* * * * *